(12) United States Patent
Chen et al.

(10) Patent No.: US 12,251,522 B1
(45) Date of Patent: Mar. 18, 2025

(54) POST-OPERATIVE INDWELLING URINARY CATHETER SUITABLE FOR MALES

(71) Applicant: Guangzhou Institute of Cancer Research, the Affiliated Cancer Hospital, Guangzhou Medical University, Guangdong (CN)

(72) Inventors: Yanfei Chen, Guangdong (CN); Guoshuo Chen, Guangdong (CN); Ling Li, Guangdong (CN); Yingwen Zhu, Guangdong (CN); Xuejin Zhu, Guangdong (CN); Sian Chen, Guangdong (CN); Jinhai Wu, Guangdong (CN)

(73) Assignee: Guangzhou Institute of Cancer Research, the Affiliated Cancer Hospital, Guangzhou Medical University, Guangdong (CN)

( * ) Notice: Subject to any disclaimer, the term of this patent is extended or adjusted under 35 U.S.C. 154(b) by 0 days.

(21) Appl. No.: 18/939,382

(22) Filed: Nov. 6, 2024

Related U.S. Application Data

(63) Continuation of application No. PCT/CN2024/121603, filed on Sep. 27, 2024.

(51) Int. Cl.
*A61M 25/00* (2006.01)
*A61M 25/10* (2013.01)

(52) U.S. Cl.
CPC ........ *A61M 25/0017* (2013.01); *A61M 25/10* (2013.01)

(58) Field of Classification Search
CPC .............. A61M 25/0017; A61M 25/10; A61M 25/1009; A61M 2025/0018; A61M 2025/0019; A61M 2025/0021; A61M 2025/0026; A61M 2025/0034; A61M 2210/1078; A61M 2210/1085; A61M 2210/1089; A61M 2210/1096
See application file for complete search history.

(56) References Cited

U.S. PATENT DOCUMENTS

| | | | |
|---|---|---|---|
| 2014/0150782 A1* | 6/2014 | Vazales | A61M 25/1018 128/202.16 |
| 2017/0021129 A1* | 1/2017 | Erbey, II | A61M 1/70 |
| 2017/0348507 A1* | 12/2017 | Erbey, II | A61M 25/04 |
| 2017/0348512 A1* | 12/2017 | Orr | A61M 1/75 |
| 2018/0185611 A1* | 7/2018 | Bonneau | A61M 25/1018 |
| 2018/0214297 A1* | 8/2018 | Hughett | A61B 5/7445 |
| 2019/0336325 A1* | 11/2019 | Lee-Sepsick | A61L 24/001 |
| 2019/0343445 A1* | 11/2019 | Burnett | A61B 5/207 |
| 2021/0205589 A1* | 7/2021 | Dong | A61M 27/002 |
| 2022/0047842 A1* | 2/2022 | Rehm | A61M 1/71 |

(Continued)

*Primary Examiner* — Philip R Wiest

(57) ABSTRACT

The present disclosure belongs to the technical field of medical devices, and in particular relates to a post-operative indwelling urinary catheter suitable for males. In view of a problem that a urinary catheter is prone to shaking due to collision, in the present disclosure, by arranging a shield, a limiting ring is rotated to adjust a connection position of a spiral tube and a chassis, and the shield is pushed to cause a fixing soft disk to be abutted against a human body, avoiding the possibility of urethral irritation or injury when an external urinary catheter I is shaken, avoiding bacterial invasion and urinary tract infection, and improving the comfort of use.

10 Claims, 7 Drawing Sheets

(56) References Cited

U.S. PATENT DOCUMENTS

| | | | |
|---|---|---|---|
| 2022/0054798 A1* | 2/2022 | Erbey, II | A61M 25/04 |
| 2024/0042120 A1* | 2/2024 | Cheng | G16H 40/63 |
| 2024/0130843 A1* | 4/2024 | Howes | A61M 25/0017 |
| 2024/0424252 A1* | 12/2024 | Kandrac | A61M 25/002 |

* cited by examiner

POST-OPERATIVE INDWELLING URINARY CATHETER SUITABLE FOR MALES

CROSS-REFERENCE TO RELATED APPLICATIONS

This application is a continuation of PCT/CN2024/121603, filed on Sep. 27, 2024, the entire contents of which are incorporated herein by reference.

TECHNICAL FIELD

The present disclosure relates to the technical field of medical devices, and in particular to a post-operative indwelling urinary catheter suitable for males.

BACKGROUND

An indwelling urinary catheter is a commonly used medical device, which is mainly used to help patients who can't urinate on their own to discharge urine. A head end of a commonly used indwelling urinary catheter is arranged with a urethral catheterization hole and an expandable and contractible hollow bladder, and a distal end of the commonly used indwelling urinary catheter is arranged with a urethral catheterization port communicated with the urethral catheterization hole and a bladder port communicated with the hollow bladder. When in use, the head end of the urinary catheter is inserted into a bladder of a patient through a urethra, normal saline or gas is introduced into the hollow bladder through the bladder port, the bladder is inflated and fixed in the bladder to define a position of the urinary catheter, ensuring that the urinary catheter can be stably inserted into the patient for a long time, and the urine of the patient is discharged through a urine outlet communicated with the urethral catheterization port.

Without being fixed, the common urinary catheter is prone to shaking due to collision. Frequent shaking may cause urethral irritation or injury, and an unstable urinary catheter is more likely to cause bacterial invasion and urinary tract infection, resulting in discomfort and pain, and reducing comfort. Therefore, a post-operative indwelling urinary catheter suitable for males is provided.

SUMMARY

The present disclosure provides a post-operative indwelling urinary catheter suitable for males to solve the problem that the urinary catheter is prone to shaking due to collision.

In order to achieve the above object, the present disclosure adopts the following technical solutions. A post-operative indwelling urinary catheter suitable for males includes a urinary catheter I. A balloon tube is sheathed and fixed to a position near a top end of a circumferential outer wall of the urinary catheter I, and a balloon ring is mounted at a top end of the balloon tube; a gas transmission tube is inserted at a position near a bottom end of a circumferential outer wall of the balloon tube, and a control valve I is sheathed and fixed to a circumferential outer wall of the gas transmission tube; a spiral tube is sheathed and fixed to a position near a bottom end of the circumferential outer wall of the balloon tube, and a limiting ring is screwed at a position near a middle of a circumferential outer wall of the spiral tube; a chassis is sheathed at a position near a top end of the circumferential outer wall of the spiral tube, and a shield is sheathed and fixed to a circumferential outer wall of the chassis; a top end of the shield is fixed to a fixing soft disk, and ventilation holes are uniformly disposed on a circumferential outer wall of the shield; a double-control mechanism is mounted at the position near a bottom end of the circumferential outer wall of the urinary catheter I, and the double-control mechanism includes a urinary catheter II; an anti-backflow mechanism is mounted at a position near a bottom end of a circumferential outer wall of the urinary catheter II, and the anti-backflow mechanism includes a urinary catheter III; and a fixing mechanism is sheathed at a position near a bottom end of a circumferential outer wall of the urinary catheter III, and the fixing mechanism includes a fixing ring.

A further arrangement of the present disclosure is as follows. The double-control mechanism includes a cut-off box, a first control mechanism is sheathed at a position near a bottom end of the circumferential outer wall of the urinary catheter I, and the control mechanism includes the cut-off box; a mounting hole is disposed at a top of the cut-off box, and the mounting hole is matched with the urinary catheter I; fixing columns are uniformly fixed to an inner wall of a top end of the cut-off box near a circumferential edge of the mounting hole, and cut-off plates are rotatably connected to circumferential outer walls of the fixing columns; positioning holes are disposed at positions near circumferential edges of bottom ends of the cut-off plates, and the positioning holes are adapted to the fixing columns; a plurality of cut-off plates constitute a circular gate plate, and movable columns are welded at positions near the circumferential edges of the bottom ends of the cut-off plates; connecting arms are rotatably connected to circumferential outer walls of the movable columns, and insertion rods are inserted at ends of upper surfaces of the connecting arms away from the movable columns; a bottom ring is fixed to a position near a top end of a circumferential inner wall of the cut-off box, and progress grooves are uniformly disposed at a bottom end of the bottom ring; and the progress grooves are slidably connected to the insertion rods, and the progress grooves correspond to the insertion rods one by one.

A further arrangement of the present disclosure is as follows. A sealing disk II is fixed on a circumferential inner wall of the cut-off box near bottom ends of the connecting arms, and progress holes II are uniformly disposed at a position near a circumferential edge of an upper surface of the sealing disk II; the progress holes II correspond to the progress grooves one by one, and the insertion rods pass through the progress holes II; a loading tube is fixed to a position away from a center of a circle of a bottom end of the sealing disk II by means of bolts, and a safety tube is inserted on a circumferential inner wall of the loading tube; and a sealing disk I is fixed to a bottom end of the cut-off box by means of bolts, progress holes I are uniformly disposed at positions near a circumferential edge of an upper surface of the sealing disk I, the progress holes I correspond to the progress holes II one by one, and the insertion rods pass through the progress holes I.

A further arrangement of the present disclosure is as follows. An adjustment ring is rotatably connected to a circumferential outer wall of the cut-off box, insertion holes are uniformly disposed at a bottom end of the adjustment ring, several insertion holes are all plugged with connecting columns, and the connecting columns correspond to the insertion rods one by one; and connecting blocks are sleeved at positions near bottom ends of circumferential outer walls of the connecting columns, connecting holes are disposed on sides of upper surfaces of the connecting blocks away from the connecting columns, and the connecting holes are connected to the insertion rods.

A further arrangement of the present disclosure is as follows. A transition tube is sheathed at a portion near a bottom end of a circumferential outer wall of the safety tube, and second control mechanisms with the same structure as the first control mechanism and mutually symmetrical are mounted at portions near a bottom end of a circumferential inner wall of the transition tube; a cleaning tube is inserted at a portion near one side of the circumferential outer wall of the transition tube, and a control valve II is sheathed and fixed to a circumferential outer wall of the cleaning tube; and a medicine feeding tube is inserted at a portion near the other side of the circumferential outer wall of the transition tube, and a control valve III is sheathed and fixed to a circumferential outer wall of the medicine feeding tube.

A further arrangement of the present disclosure is as follows. The anti-backflow mechanism includes a urinary catheter II, the urinary catheter II is inserted at a bottom end of the cut-off box of the second control mechanisms, and a circumferential outer wall of the urinary catheter II is sheathed with a safety tube; a clamping plate is clamped and fixed to a position near a top end of a circumferential inner wall of the safety tube, and a loading ring is fixed to a position off the center of the circle of a bottom end of the clamping plate via bolts; and a supporting spring is fixed to a position near a middle of a bottom end of the clamping plate, and a bottom end of the supporting spring is connected to a flow stopping plate in a transition manner.

A further arrangement of the present disclosure is as follows. Limiting columns are uniformly inserted at a position near a circumferential inner wall of a bottom end of the loading ring, and anti-drop plates are uniformly fixed to bottom ends of the limiting columns.

A further arrangement of the present disclosure is as follows. A loading column is fixed to a position near a center of a bottom end of the clamping plate, a floating ring is sleeved and fixed to a circumferential outer wall of the loading column, and the urinary catheter III is inserted at a position near a bottom end of the circumferential inner wall of the safety tube.

A further arrangement of the present disclosure is as follows. The fixing mechanism includes a first fixing group, and the first fixing group includes the fixing ring; the fixing ring is sheathed at a position near a top end of a circumferential outer wall of the urinary catheter III, and extension rods I are uniformly inserted at a bottom end of the fixing ring; limiting blocks I are fixed to ends of the extension rods I away from the fixing ring, and extension rods II are inserted at positions near sides of top ends of the limiting blocks I; limiting blocks II are welded to ends of the extension rods II near the fixing ring, and the limiting blocks II and the extension rods I are slidingly inserted; ends of several extension rods II away from the fixing ring are inserted with same fixed disks, annular grooves are disposed at positions near circumferential edges of bottom ends of the fixed disks, and one of the annular grooves are rotatably connected to two symmetrical side plates; and ends of the side plates are welded with the same bottom plates, and bottom ends of the two side plates are connected to a second fixing group which has the same structure as the first fixing group and is symmetrical with each other via a hinge.

A further arrangement of the present disclosure is as follows. A position near a bottom of one end of one of the side plates of the first fixing group is rotatably connected to a support column, an insertion tube is welded at a top end of the support column, and a position near one side of a top end of the insertion tube is screwed to a limiting rod; and a position near a bottom of one end of one of the side plates of the second fixing group is rotatably connected to a support column, a top end of the support column is welded with an insertion plate, and the insertion plate is adapted to the insertion tube.

In summary, the beneficial effects in the solutions are as follows.

1. By arranging the shield, the limiting ring is rotated to adjust a connection position of the spiral tube and the chassis, the shield is pushed to cause the fixing soft disk to be abutted against a human body, avoiding the possibility of urethral irritation or injury when an external urinary catheter I is shaken, avoiding bacterial invasion and urinary tract infection, and improving the comfort of use.

2. By arranging the cut-off plates, urination can be stopped in time, and a bladder can normally store urine, avoiding the possible effect of long-term catheterization on the natural function of the bladder, and avoiding the gradual decrease of the urination capacity of the bladder.

3. By arranging the flow stopping plate, urine presses the flow stopping plate when urinating, and the flow stopping plate is separated from the loading ring to form a channel, completing the flow of urine; and the flow stopping plate is pressed against the loading ring when the urine flows back, and the channel is closed to prevent the back flow.

Figure 1:
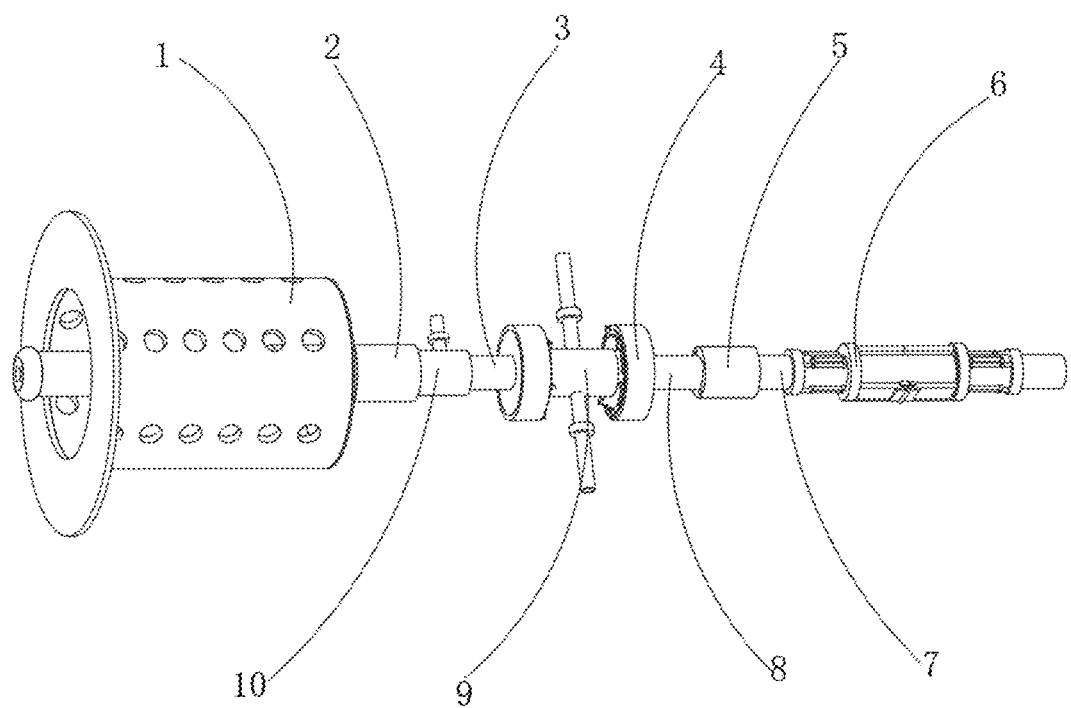
FIG. 1 is an overall schematic diagram of a post-operative indwelling urinary catheter suitable for males proposed by the present disclosure.
Figure 2:
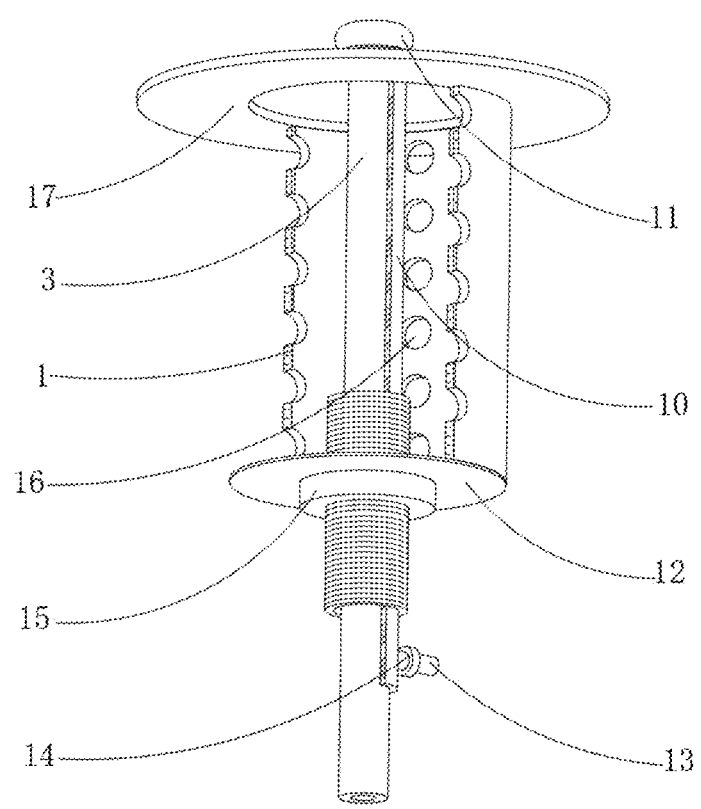
FIG. 2 is a schematic structural diagram of a shield of the post-operative indwelling urinary catheter suitable for males proposed by the present disclosure.

Reference numerals and denotations thereof. 1—shield; 2—spiral tube; 3—urinary catheter I; 4—adjustment ring; 401—insertion hole; 5—protective tube; 6—fixing disk; 601—annular groove; 7—urinary catheter III; 8—urinary catheter II; 9—transition tube; 10—balloon tube; 11—balloon ring; 12—chassis; 13—gas transmission tube; 14—control valve I; 15—limiting ring; 16—ventilation hole; 17—fixing soft disk; 18—cleaning tube; 19—control valve II; 20—cut-off box; 21—medicine feeding tube; 22—control valve III; 23—cut-off plate; 2301—positioning hole; 24—fixing column; 25—connecting arm; 26—sealing disk I; 2601—progress hole I; 27—loading tube; 28—connecting column; 29—insertion rod; 30—bottom ring; 3001—progress groove; 31—sealing disk II; 3101—progress hole II; 32—safety tube; 33—movable column;

34—connecting block; 35—connecting hole; 36—clamping plate; 37—supporting spring; 38—loading ring; 39—flow stopping plate; 40—limiting column; 41—anti-drop plate; 42—loading column; 43—floating ring; 44—fixing ring; 45—extension rod I; 46—limiting block I; 47—bottom plate; 48—side plate; 49—insertion plate; 50—limiting rod; 51—insertion tube; 52—extension rod II; and 53—limiting block II.

DETAILED DESCRIPTION

Technical solutions in the examples of the present disclosure will be described clearly and completely in the following with reference to the attached drawings in the examples of the present disclosure. Obviously, all the described examples are only some, rather than all examples of the present disclosure.

In the present examples, with reference to FIGS. 1-7, a post-operative indwelling urinary catheter suitable for males includes a urinary catheter I 3. A balloon tube 10 is sheathed and fixed to a position near a top end of a circumferential outer wall of the urinary catheter I 3, and a balloon ring 11 is mounted at a top end of the balloon tube 10; a gas transmission tube 13 is inserted at a position near a bottom end of a circumferential outer wall of the balloon tube 10, and a control valve I 14 is sheathed and fixed to a circumferential outer wall of the gas transmission tube 13; a spiral tube 2 is sheathed and fixed to a position near a bottom end of the circumferential outer wall of the balloon tube 10, and a limiting ring 15 is screwed at a position near a middle of a circumferential outer wall of the spiral tube 2; a chassis 12 is sheathed at a position near a top end of the circumferential outer wall of the spiral tube 2, and a shield 1 is sheathed and fixed to a circumferential outer wall of the chassis 12; a top end of the shield 1 is fixed to a fixing soft disk 17, and ventilation holes 16 are uniformly disposed on a circumferential outer wall of the shield 1; a double-control mechanism is mounted at the position near a bottom end of the circumferential outer wall of the urinary catheter I 3, and the double-control mechanism includes a urinary catheter II 8; an anti-backflow mechanism is mounted at a position near a bottom end of a circumferential outer wall of the urinary catheter II 8, and the anti-backflow mechanism includes a urinary catheter III 7; and a fixing mechanism is sheathed at a position near a bottom end of a circumferential outer wall of the urinary catheter III 7, and the fixing mechanism includes a fixing ring 44. The limiting ring 15 is rotated to adjust a connection position of the spiral tube 2 and the chassis 12, the shield 1 is pushed to cause the fixing soft disk 17 to be abutted against a human body, avoiding the possibility of urethral irritation or injury when an external urinary catheter I 3 is shaken, avoiding bacterial invasion and urinary tract infection, and improving the comfort of use.

Figure 3:
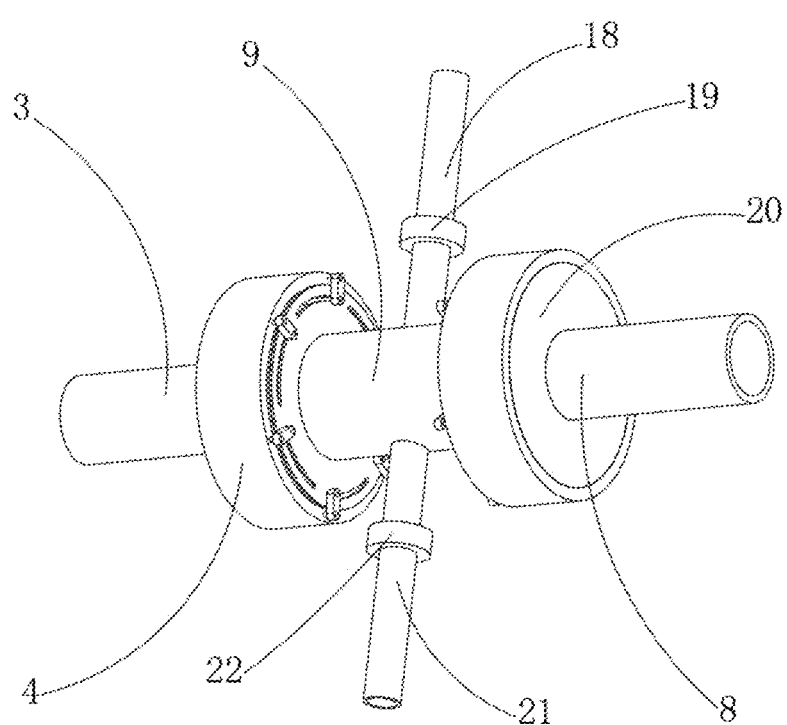
FIG. 3 is a schematic structural diagram of a double-control mechanism of the post-operative indwelling urinary catheter suitable for males proposed by the present disclosure.
Figure 4:
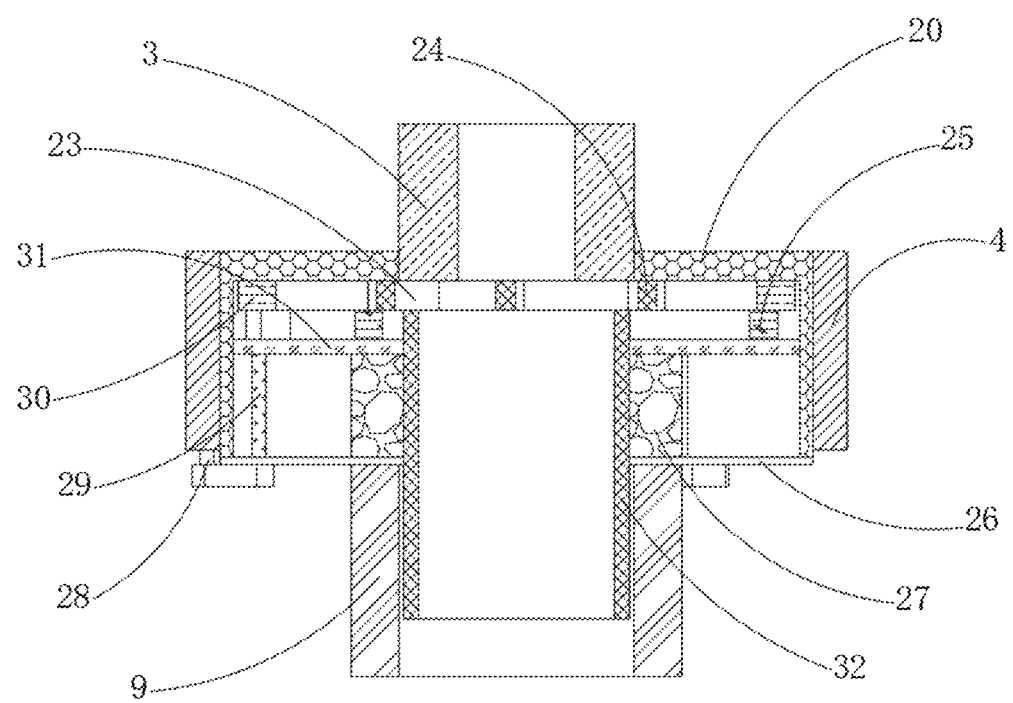
FIG. 4 is a schematic structural cross-sectional view of the double-control mechanism of the post-operative indwelling of urinary catheter suitable for males proposed by the present disclosure.
Figure 5:
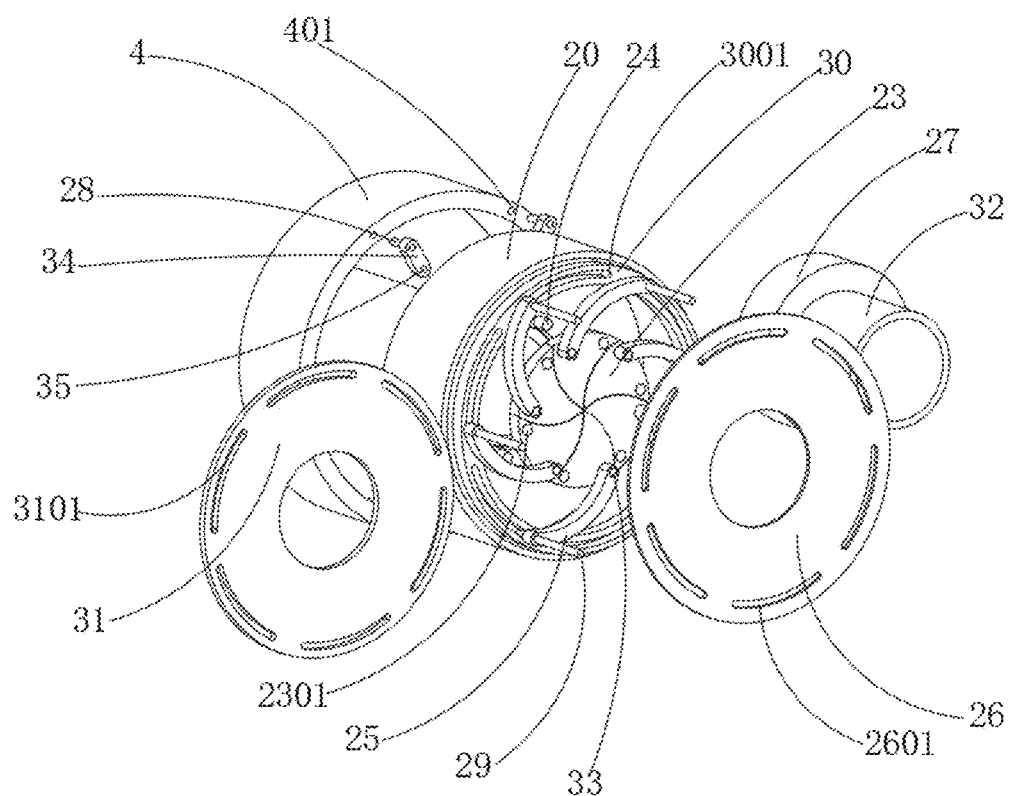
FIG. 5 is an explosive structural view of the double-control mechanism of the post-operative indwelling urinary catheter suitable for males proposed by the present disclosure.

With reference to FIGS. 3, 4 and 5, the double-control mechanism includes a cut-off box 20, a first control mechanism is sheathed at a position near the bottom end of the circumferential outer wall of the urinary catheter I 3, and the control mechanism includes the cut-off box 20; a mounting hole is disposed at a top of the cut-off box 20, and the mounting hole is matched with the urinary catheter I 3; fixing columns 24 are uniformly fixed to an inner wall of a top end of the cut-off box 20 near a circumferential edge of the mounting hole, and cut-off plates 23 are rotatably connected to circumferential outer walls of the fixing columns 24; and positioning holes 2301 are disposed at positions near circumferential edges of bottom ends of the cut-off plates 23, and the positioning holes 2301 are adapted to the fixing columns 24. A plurality of cut-off plates 23 constitute a circular gate plate, and movable columns 33 are welded at positions near the circumferential edges of the bottom ends of the cut-off plates 23; connecting arms 25 are rotatably connected to circumferential outer walls of the movable columns 33, and insertion rods 29 are inserted at ends of upper surfaces of the connecting arms 25 away from the movable columns 33; a bottom ring 30 is fixed to a position near a top end of a circumferential inner wall of the cut-off box 20, and progress grooves 3001 are uniformly disposed at a bottom end of the bottom ring 30; and the progress grooves 3001 are slidably connected to the insertion rods 29, and the progress grooves 3001 correspond to the insertion rods 29 one by one. The insertion rods 29 are slid along the progress grooves 3001 to control the closure or dispersion of the cut-off plates 23. A sealing disk II 31 is fixed on a circumferential inner wall of the cut-off box 20 near bottom ends of the connecting arms 25, and progress holes II 3101 are uniformly disposed at a position near a circumferential edge of an upper surface of the sealing disk II 31; the progress holes II 3101 correspond to the progress grooves 3001 one by one, and the insertion rods 29 pass through the progress holes II 3101; a loading tube 27 is fixed to a position away from a centre of a circle of a bottom end of the sealing disk II 31 by means of bolts, and a safety tube 32 is inserted on a circumferential inner wall of the loading tube 27; a sealing disk I 26 is fixed to a bottom end of the cut-off box 20 by means of bolts, progress holes I 2601 are uniformly disposed at positions near a circumferential edge of an upper surface of the sealing disk I 26, the progress holes I 2601 correspond to the progress holes II 3101 one by one, and the insertion rods 29 pass through the progress holes I 2601; an adjustment ring 4 is rotatably connected to a circumferential outer wall of the cut-off box 20, insertion holes 401 are uniformly disposed at a bottom end of the adjustment ring 4, several insertion holes 401 are all plugged with connecting columns 28, and the connecting columns 28 correspond to the insertion rods 29 one by one; and connecting blocks 34 are sleeved at positions near bottom ends of circumferential outer walls of the connecting columns 28, connecting holes 35 are disposed on sides of upper surfaces of the connecting blocks 34 away from the connecting columns 28, and the connecting holes 35 are connected to the insertion rods 29. The adjustment ring 4 is rotated to drive the insertion rods 29 to rotate to complete the closure or dispersion of the cut-off plates 23. By arranging the cut-off plates 23, urination can be stopped in time, and a bladder can normally store urine, avoiding the possible effect of long-term catheterization on the natural function of the bladder, and avoiding the gradual decrease of the urination capacity of the bladder.

With reference to FIGS. 3 and 4, a transition tube 9 is sheathed at a portion near a bottom end of a circumferential outer wall of the safety tube 32, and second control mechanisms with the same structure as the first control mechanism and mutually symmetrical are mounted at portions near a bottom end of a circumferential inner wall of the transition tube 9; a cleaning tube 18 is inserted at a portion near one side of the circumferential outer wall of the transition tube 9, and a control valve II 19 is sheathed and fixed to a circumferential outer wall of the cleaning tube 18; and a medicine feeding tube 21 is inserted at a portion near the other side of the circumferential outer wall of the transition tube 9, and a control valve III 22 is sheathed and fixed to a circumferential outer wall of the medicine feeding tube 21. By arranging two cut-off plates 23, water can be injected to clean the urinary catheter, keeping the urinary catheter clean, allowing medicines to be injected directly into a urethra or a bladder, and enabling local treatment and more precise control of symptoms.

Figure 6:
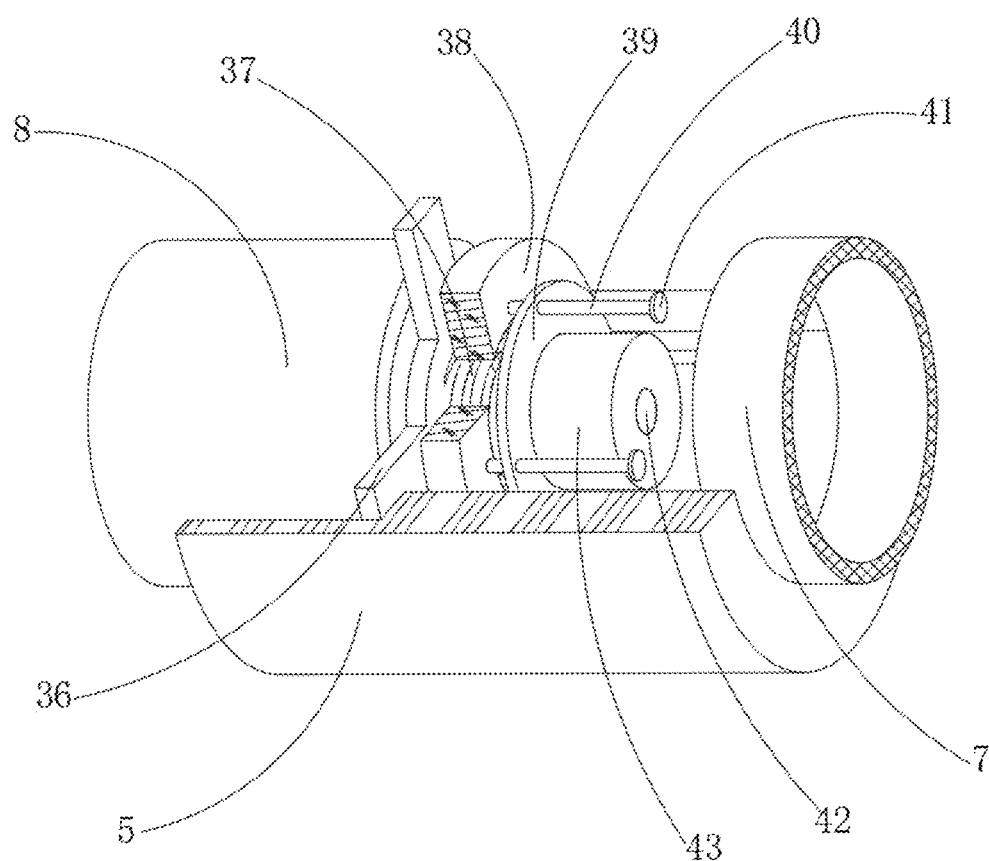
FIG. 6 is a schematic structural diagram of an anti-backflow mechanism of the post-operative indwelling urinary catheter suitable for males proposed by the present disclosure.

With reference to FIG. 6, the anti-backflow mechanism includes a urinary catheter II 8, the urinary catheter II 8 is inserted at a bottom end of the cut-off box 20 of the second control mechanisms, and a circumferential outer wall of the urinary catheter II 8 is sheathed with a protective tube 5; a clamping plate 36 is clamped and fixed to a position near a top end of a circumferential inner wall of the protective tube 5, and a loading ring 38 is fixed to a position off the center of the circle of a bottom end of the clamping plate 36 via bolts; a supporting spring 37 is fixed to a position near a middle of a bottom end of the clamping plate 36, and a bottom end of the supporting spring 37 is connected to a flow stopping plate 39 in a transition manner; limiting columns 40 are uniformly inserted at a position near a circumferential inner wall of a bottom end of the loading ring 38, and anti-drop plates 41 are uniformly fixed to bottom ends of the limiting columns 40; a loading column 42 is fixed to a position near a center of a bottom end of the clamping plate 36, a floating ring 43 is sleeved and fixed to a circumferential outer wall of the loading column 42, and the urinary catheter III 7 is inserted at a position near a bottom end of the circumferential inner wall of the protective tube 5. By arranging the flow stopping plate 39, urine presses the flow stopping plate 39 when urinating, and the flow stopping plate 39 is separated from the loading ring 38 to form a channel, completing the flow of urine; and the flow stopping plate 39 is pressed against the loading ring 38 when the urine flows back, and the channel is closed to prevent the back flow.

Figure 7:
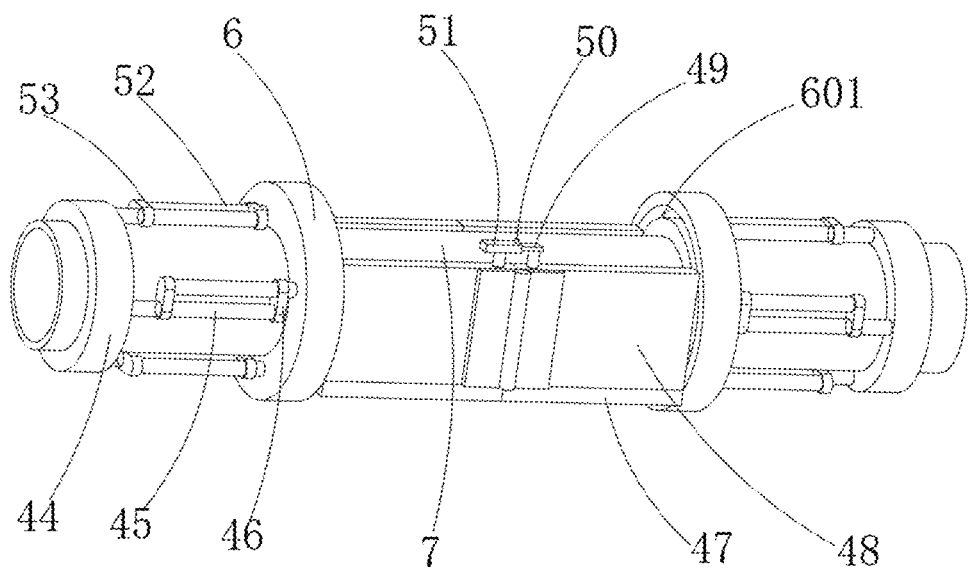
FIG. 7 is a schematic structural diagram of a fixing mechanism of the post-operative indwelling urinary catheter suitable for males proposed by the present disclosure.

With reference to FIG. 7, the fixing mechanism includes a first fixing group, and the first fixing group includes the fixing ring 44; the fixing ring 44 is sheathed at a position near a top end of a circumferential outer wall of the urinary catheter III 7, and extension rods I 45 are uniformly inserted at a bottom end of the fixing ring 44; limiting blocks I 46 are fixed to ends of the extension rods I 45 away from the fixing ring 44, and extension rods II 52 are inserted at positions near sides of top ends of the limiting blocks I 46; and limiting blocks II 53 are welded to ends of the extension rods II 52 near the fixing ring 44, and the limiting blocks II 53 and the extension rods I 45 are slidingly inserted. When the extension rods I 45 and the extension rods II 52 move relative to each other, a fixed distance is shortened, and when the extension rods I 45 and the extension rods II 52 move opposite to each other, the fixed distance is lengthened. Ends of several extension rods II 52 away from the fixing ring 44 are inserted with same fixed disks 6, annular grooves 601 are disposed at positions near circumferential edges of bottom ends of the fixed disks 6, and the annular grooves 601 are rotatably connected to two symmetrical side plates 48; ends of the side plates 48 are welded with the same bottom plates 47, and bottom ends of the two side plates 48 are connected to a second fixing group which has the same structure as the first fixing group and is symmetrical with each other via a hinge; a position near a bottom of one end of one of the side plates 48 of the first fixing group is rotatably connected to a support column, an insertion tube 51 is welded at a top end of the support column, and a position near one side of a top end of the insertion tube 51 is screwed to a limiting rod 50; and a position near a bottom of one end of one of the side plates 48 of the second fixing group is rotatably connected to a support column, a top end of the support column is welded with an insertion plate 49, and the insertion plate 49 is adapted to the insertion tube 51. By arranging the fixing mechanism, the urinary catheter III 7 can be protected, an angle of the urinary catheter III 7 can also be changed, and a fixing can be performed at a specific position, preventing damage to the urinary catheter III 7.

When the present disclosure is used, firstly, the urinary catheter I 3 and the balloon tube 10 are extended into the bladder of a patient, inflation of the balloon ring 11 is completed via the gas transmission tube 13, fixing the balloon ring 11 in the patient's body, and preventing the urinary catheter I 3 from falling off, and the limiting ring 15 is rotated to push the shield 1 to cause the fixing soft disk 17 to be abutted against the patient, completing external fixation, and avoiding shaking of the urinary catheter I 3 and stimulating the urethra. When urination is not required, the adjustment ring 4 is rotated to close the cut-off plates 23. When injecting the medicines, the cut-off plate 23 at the top end is scattered, the cut-off plate 23 at the bottom end is closed, the medicines are injected along the medicine feeding tube 21, and the medicines enter the urethra and the bladder along the urinary catheter I 3. When the urinary catheter I 3 is necessary to be cleaned, the cut-off plate 23 at the top end is closed, the cut-off plate 23 at the bottom end is scattered, a cleaning liquid is injected along the cleaning tube 18, and the cleaning liquid flows out along the urinary catheter II 8 to complete the cleaning of the tubeline. When a urine bag is collided and the urine flows back into the protective tube 5, the floating ring 43 is soaked to generate buoyancy and push the flow stopping plate 39 to be attached to the loading ring 38, and the flow channel is closed and the backflow is prevented. When the urinary catheter III 7 is touched by surrounding for many times, the fixing ring 44 and the side plate 48 surround the urinary catheter III 7 to prevent the urinary catheter III 7 from being damaged by direct contact with foreign objects, and the extension rods I 45 and the extension rods II 52 move relatively to shorten the fixed distance and move reversely to extend the fixed distance. When the limiting rods 50 are pulled out, two adjacent side plates 48 are rotated along the hinge to an appropriate fixed angle, and the limiting rods 50 are inserted to a fixed angle.

All the above are only the preferred examples of the present disclosure, but the scope of protection of the present disclosure is not limited to this. Within the technical scope disclosed by the present disclosure, any equivalent replacements or changes made by those skilled familiar with the technical field according to the technical solution and inventive concept of the present disclosure are to be included in the scope of protection of the present disclosure.

The invention claimed is:

1. A post-operative indwelling urinary catheter suitable for males, comprising a urinary catheter I (3), wherein a balloon tube (10) is sheathed and fixed to a position near a top end of a circumferential outer wall of the urinary catheter I (3), and a balloon ring (11) is mounted at a top end of the balloon tube (10); a gas transmission tube (13) is inserted at a position near a bottom end of a circumferential outer wall of the balloon tube (10), and a control valve I (14) is sheathed and fixed to a circumferential outer wall of the gas transmission tube (13); a spiral tube (2) is sheathed and fixed to a position near a bottom end of the circumferential outer wall of the balloon tube (10), and a limiting ring (15) is screwed at a position near a middle of a circumferential outer wall of the spiral tube (2); a chassis (12) is sheathed at a position near a top end of the circumferential outer wall of the spiral tube (2), and a shield (1) is sheathed and fixed to a circumferential outer wall of the chassis (12); a top end of the shield (1) is fixed to a fixing soft disk (17), and ventilation holes (16) are uniformly disposed on a circumferential outer wall of the shield (1); a double-control mechanism is mounted at the position near a bottom end of the circumferential outer wall of the urinary catheter I (3), and the double-control mechanism comprises a urinary catheter II (8); an anti-backflow mechanism is mounted at a position near a bottom end of a circumferential outer wall of the urinary catheter II (8), and the anti-backflow mechanism comprises a urinary catheter III (7); and a fixing mechanism is sheathed at a position near a bottom end of a circumferential outer wall of the urinary catheter III (7), and the fixing mechanism comprises a fixing ring (44).

2. The post-operative indwelling urinary catheter suitable for males according to claim 1, wherein the double-control mechanism comprises a cut-off box (20), a first control mechanism is sheathed at a position near the bottom end of the circumferential outer wall of the urinary catheter I (3), and the control mechanism comprises the cut-off box (20); a mounting hole is disposed at a top of the cut-off box (20), and the mounting hole is matched with the urinary catheter I (3); fixing columns (24) are uniformly fixed to an inner wall of a top end of the cut-off box (20) near a circumferential edge of the mounting hole, and cut-off plates (23) are rotatably connected to circumferential outer walls of the fixing columns (24); positioning holes (2301) are disposed at positions near circumferential edges of bottom ends of the cut-off plates (23), and the positioning holes (2301) are adapted to the fixing columns (24); a plurality of cut-off plates (23) constitute a circular gate plate, and movable columns (33) are welded at positions near the circumferential edges of the bottom ends of the cut-off plates (23); connecting arms (25) are rotatably connected to circumferential outer walls of the movable columns (33), and insertion rods (29) are inserted at ends of upper surfaces of the connecting arms (25) away from the movable columns (33); a bottom ring (30) is fixed to a position near a top end of a circumferential inner wall of the cut-off box (20), and progress grooves (3001) are uniformly disposed at a bottom end of the bottom ring (30); and the progress grooves (3001) are slidably connected to the insertion rods (29), and the progress grooves (3001) correspond to the insertion rods (29) one by one.

3. The post-operative indwelling urinary catheter suitable for males according to claim 2, wherein a sealing disk II (31) is fixed on a circumferential inner wall of the cut-off box (20) near bottom ends of the connecting arms (25), and progress holes II (3101) are uniformly disposed at a position near a circumferential edge of an upper surface of the sealing disk II (31); the progress holes II (3101) correspond to the progress grooves (3001) one by one, and the insertion rods (29) pass through the progress holes II (3101); a loading tube (27) is fixed to a position away from a center of a circle of a bottom end of the sealing disk II (31) by means of bolts, and a safety tube (32) is inserted at a circumferential inner wall of the loading tube (27); and a sealing disk I (26) is fixed to a bottom end of the cut-off box (20) by means of bolts, progress holes I (2601) are uniformly disposed at positions near a circumferential edge of an upper surface of the sealing disk I (26), the progress holes I (2601) correspond to the progress holes II (3101) one by one, and the insertion rods (29) pass through the progress holes I (2601).

4. The post-operative indwelling urinary catheter suitable for males according to claim 3, wherein an adjustment ring (4) is rotatably connected to a circumferential outer wall of the cut-off box (20), insertion holes (401) are uniformly disposed at a bottom end of the adjustment ring (4), several insertion holes (401) are all plugged with connecting columns (28), and the connecting columns (28) correspond to the insertion rods (29) one by one; and connecting blocks (34) are sleeved at positions near bottom ends of circumferential outer walls of the connecting columns (28), connecting holes (35) are disposed on sides of upper surfaces of the connecting blocks (34) away from the connecting columns (28), and the connecting holes (35) are connected to the insertion rods (29).

5. The post-operative indwelling urinary catheter suitable for males according to claim 4, wherein a transition tube (9) is sheathed at a portion near a bottom end of a circumferential outer wall of the safety tube (32), and second control mechanisms with the same structure as the first control mechanism and mutually symmetrical are mounted at portions near a bottom end of a circumferential inner wall of the transition tube (9); a cleaning tube (18) is inserted at a portion near one side of the circumferential outer wall of the transition tube (9), and a control valve II (19) is sheathed and fixed to a circumferential outer wall of the cleaning tube (18); and a medicine feeding tube (21) is inserted at a portion near the other side of the circumferential outer wall of the transition tube (9), and a control valve III (22) is sheathed and fixed to a circumferential outer wall of the medicine feeding tube (21).

6. The post-operative indwelling urinary catheter suitable for males according to claim 5, wherein the anti-backflow mechanism comprises a urinary catheter II (8), the urinary catheter II (8) is inserted at a bottom end of the cut-off box (20) of the second control mechanism, and a circumferential outer wall of the urinary catheter II (8) is sheathed with a protective tube (5); a clamping plate (36) is clamped and fixed to a position near a top end of a circumferential inner wall of the protective tube (5), and a loading ring (38) is fixed to a position off the center of the circle of a bottom end of the clamping plate (36) via bolts; and a supporting spring (37) is fixed to a position near a middle of a bottom end of the clamping plate (36), and a bottom end of the supporting spring (37) is connected to a flow stopping plate (39) in a transition manner.

7. The post-operative indwelling urinary catheter suitable for males according to claim 6, wherein limiting columns (40) are uniformly inserted at a position near a circumferential inner wall of a bottom end of the loading ring (38), and anti-drop plates (41) are uniformly fixed to bottom ends of the limiting columns (40).

8. The post-operative indwelling urinary catheter suitable for males according to claim 6, wherein a loading column (42) is fixed to a position near a center of a bottom end of the clamping plate (36), a floating ring (43) is sleeved and fixed to a circumferential outer wall of the loading column (42), and the urinary catheter III (7) is inserted at a position near a bottom end of the circumferential inner wall of the protective tube (5).

9. The post-operative indwelling urinary catheter suitable for males according to claim 8, wherein the fixing mechanism comprises a first fixing group, and the first fixing group comprises the fixing ring (44); the fixing ring (44) is sheathed at a position near a top end of a circumferential outer wall of the urinary catheter III (7), and extension rods I (45) are uniformly inserted at a bottom end of the fixing ring (44); limiting blocks I (46) are fixed to ends of the extension rods I (45) away from the fixing ring (44), and extension rods II (52) are inserted at positions near sides of top ends of the limiting blocks I (46); limiting blocks II (53) are welded to ends of the extension rods II (52) near the fixing ring (44), and the limiting blocks II (53) and the extension rods I (45) are slidingly inserted; ends of several extension rods II (52) away from the fixing ring (44) are inserted with same fixing disks (6), annular grooves (601) are disposed at positions near circumferential edges of bottom ends of the fixing disks (6), and the annular grooves (601) are rotatably connected to two symmetrical side plates (48); and ends of the side plates (48) are welded with the same bottom plates (47), and bottom ends of the two side plates (48) are connected to a second fixing group which has the same structure as the first fixing group and is symmetrical with each other via a hinge.

10. The post-operative indwelling urinary catheter suitable for males according to claim 9, wherein a position near a bottom of one end of one of the side plates (48) of the first fixing group is rotatably connected to a support column, an insertion tube (51) is welded at a top end of the support column, and a position near one side of a top end of the insertion tube (51) is screwed to a limiting rod (50); and a position near a bottom of one end of one of the side plates (48) of the second fixing group is rotatably connected to a support column, a top end of the support column is welded with an insertion plate (49), and the insertion plate (49) is adapted to the insertion tube (51).

\* \* \* \* \*